United States Patent [19]

Colle et al.

[11] Patent Number: 5,041,451
[45] Date of Patent: Aug. 20, 1991

[54] TETRAHYDROISOQUINOLINE AND TETRAHYDROTHIENO DERIVATIVES

[75] Inventors: Roberto Colle; Giuseppe Giardina, both of Milan, Italy

[73] Assignee: Dr. Lo. Zambelletti SpA, Italy

[21] Appl. No.: 440,883

[22] Filed: Nov. 22, 1989

[30] Foreign Application Priority Data

Nov. 24, 1988 [GB] United Kingdom ............... 8827479

[51] Int. Cl.$^5$ .................. A61K 31/44; C07D 217/00; C07D 471/02
[52] U.S. Cl. ........................... 514/301; 546/114; 546/115; 546/118; 546/119; 546/139; 546/146; 548/453; 548/482; 514/299; 514/300; 514/302; 514/303; 514/307
[58] Field of Search ............... 546/146, 114, 115, 118, 546/119, 139; 514/299, 300, 301, 302, 303; 548/453, 482

[56] References Cited

U.S. PATENT DOCUMENTS 3,985,881 10/1976 Mehrhof et al. .................. 546/146
3,994,891 11/1976 Hughes et al. .................... 546/146

FOREIGN PATENT DOCUMENTS 0104604 4/1984 European Pat. Off. ............ 546/146
0232989 8/1987 European Pat. Off. ............ 546/146
0330360 8/1989 European Pat. Off. ............ 546/146
0330469 8/1989 European Pat. Off. ............ 546/146
0333427 9/1989 European Pat. Off. ............ 546/146
2290206 6/1976 France ............................... 546/146

Primary Examiner—Mary C. Lee
Assistant Examiner—Joseph K. McKane
Attorney, Agent, or Firm—Rosenman & Colin

[57] ABSTRACT

A compound, or a solvate or salt thereof, of formula (I):

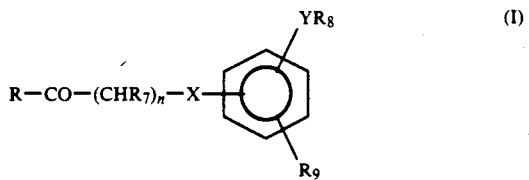

in which R represents a group of formula (II)

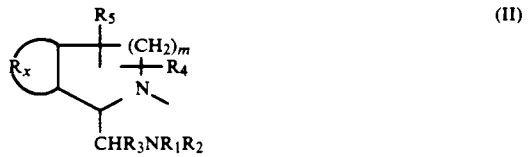

in which
$R_x$ is the remainder of a heterocyclic group, or an optionally substituted phenyl group;
$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group, optionally substituted with a hetero-atom;
$R_3$ is hydrogen, $C_{1-6}$ alkyl, or phenyl, or $R_3$ together with $R_1$ form a —$(CH_2)_3$— or —$(CH_2)_4$— group;
$R_4$ and $R_5$, which may be located on the same or different carbon atoms, are independently hydrogen, $C_{1-6}$ alkyl, or phenyl;
m is 1, 2 or 3;
$R_7$ is hydrogen or $C_{1-6}$ alkyl;
n is 0, 1 or 2;
X is direct bond, or O, S or $NR_6$ in which $R_6$ is hydrogen or $C_{1-6}$ alkyl;
Y is $>C=O$, $>CHOH$, $>S=O$ or $>SO_2$;
each is $R_8$ and $R_9$ is $C_{1-6}$ alkyl, or $R_8$ and $R_9$ are linked together and $R_8$ represents —$(Z)_p$— where p is 0 or 1 and Z is O, S or $NR_z$ where $R_z$ is hydrogen or $C_{1-6}$ alkyl;
and $R_9$ represents —$(CH_2)_q$— where q is an integer of from 1 to 4,
is useful for the treatment of pain or hyponatraemic disease states.

10 Claims, No Drawings

TETRAHYDROISOQUINOLINE AND TETRAHYDROTHIENO DERIVATIVES

This invention is concerned with novel heterocyclic derivatives, processes for their preparation, and their use in medicine, particularly as analgesics.

Compounds which are kappa-receptor agonists act as analgesics through interaction with kappa opioid receptors. The advantage of kappa-receptor agonists over the classical µ-receptor agonists, such as morphine, lies in their ability to cause analgesia while being devoid of morphine-like behavioural effects and addiction liability.

European Published Application No. 232989 discloses a group of isoquinoline derivatives which exhibit kappa-receptor agonism without some of the behavioural effects of morphine and morphine analogues, and which are thus of potential therapeutic utility as analgesics.

A novel class of structurally related heterocyclic derivatives, has now been discovered which also exhibit potent kappa-receptor agonism without the aforementioned undesirable behavioural effects.

Furthermore, this novel class of derivatives tend to show favourable binding affinity for spinal cord kappa-receptors, which potentially provides an opportunity to produce an analgesic effect without undesirable central effects.

The novel class of derivatives also possess diuretic activity which indicates that they are of potential use in the treatment of hyponatraemic disease states in mammals.

According to the present invention there is provided a compound, or a solvate or salt thereof, of formula (I):

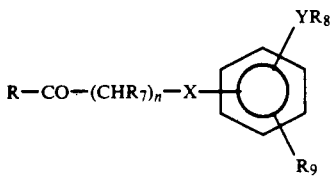

in which R represents a group of formula (II)

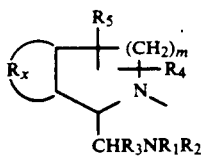

in which $R_x$ is the remainder of a heterocyclic group, or an optionally substituted phenyl group;

$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group, optionally substituted with a hetero-atom;

$R_3$ is hydrogen, $C_{1-6}$ alkyl, preferably methyl or ethyl, or phenyl, or $R_3$ together with $R_1$ form a —(CH$_2$)$_3$— or —(CH$_2$)$_4$— group;

$R_4$ and $R_5$, which may be located on the same or different carbon atoms, are independently hydrogen, $C_{1-6}$ alkyl, preferably methyl or ethyl, or phenyl; m is 1, 2 or 3, preferably 2;

$R_7$ is hydrogen or $C_{1-6}$ alkyl, such as methyl or ethyl; n is 0, 1 or 2 preferably 1;

X is direct bond, or O, S or NR$_6$ in which R$_6$ is hydrogen or $C_{1-6}$ alkyl, preferably a direct bond and preferably linked in the meta- or para- position with respect to YR$_8$ or R$_9$;

Y is >C=O, >CHOH, >S=O or >SO$_2$; each of R$_8$ and R$_9$ is $C_{1-6}$ alkyl, or R$_8$ and R$_9$ are linked together and R$_8$ represents —(Z)$_p$— where p is 0 or 1 and Z is O, S or NR$_z$ where R$_z$ is hydrogen or $C_{1-6}$ alkyl, and R$_9$ represents —(CH$_2$)$_q$— where q is an integer of from 1 to 4, preferably 2 or 3.

When $R_x$ forms an optionally substituted phenyl ring, examples of substituents are one or more of $C_{1-6}$ alkyl, preferably methyl, halogen, hydroxy, $C_{1-6}$ alkoxy, thiol or $C_{1-6}$ alkyl thio. Suitably $R_x$ represents unsubstituted phenyl.

When $R_x$ forms a heterocyclic group, it may be a single or fused ring group, preferably having aromatic character, containing from 5 to 12 ring atoms and comprising up to four hetero-atoms in the or each ring selected from oxygen, nitrogen and sulphur.

When $R_x$ forms a fused two ring system, one or both rings may be aromatic in character. Suitably one of the rings is aromatic and the other is non-aromatic.

When $R_x$ is a single ring heterocyclic group, examples are thienyl, furyl, pyrryl, imidazolyl, pyrazolyl, thiazolyl and pyridyl; and when $R_x$ is a fused ring heterocyclic group, examples are benzofuranyl, benzo thienyl, indolyl and quinolyl.

A preferred sub-group of formula (I) is a group of formula (Ia)

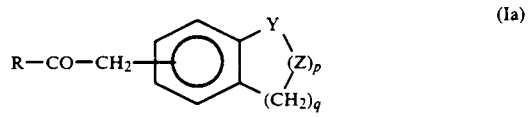

in which Y, Z, R, p, q and the position of —CH$_2$— are as defined in formula (I).

Preferably, q is 2 when Z is oxygen and p is 1, and q is 3 when p is 0.

A further preferred sub-group of formula (I) is the group of formula (Ib)

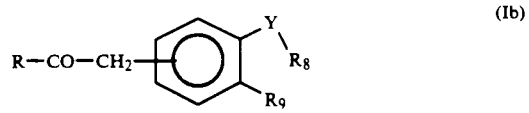

in which R is as defined in formula (I) and Y is C=O or CHOH, each of R$_8$ and R$_9$ is $C_{1-6}$ alkyl, preferably methyl, and the position of —CH$_2$— is as defined in formula (I)

The $C_{1-6}$ alkyl groups mentioned above may be either straight or branched chain and examples are methyl, ethyl, propyl, n-butyl, n-pentyl or n-hexyl, preferably methyl.

Examples of $C_{2-6}$ alkenyl groups are 1- and 2-propenyl; an example of a $C_{3-6}$ cycloalkyl group is cyclopropyl, and an example of a $C_{4-12}$ cycloalkylalkyl group is cyclopropyl methyl.

When $R_1$ and $R_2$ together form a linear or branched polymethylene group, examples are propylene, butylene, pentylene or hexylene, preferably butylene or 1-methyl-butylene. As an alkenylene group, $R_1$-$R_2$ may be typically —$CH_2$—$CH$=$CH$—$CH_2$—. Examples of hetero-atoms are oxygen and sulphur, particularly oxygen, and a suitable hetero-atom substituted polymethylene group is —$CH_2CH_2OCH_2CH_2$—.

A particularly preferred group of compounds of formula (I) are those in which $R_x$ represents phenyl or mono- or di- hydroxy substituted phenyl, or represents thieno.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

Examples of compounds of the invention are:
1-(pyrrolidin-1-yl)methyl-2-(1-oxo-3,4-dihydro-(2H)-1 naphth-6-yl)acetyl-1,2,3,4-tetrahydroisoquinoline;
1-(piperidin-1-yl)methyl-2-(1-oxo-3,4-dihydro-(2H)-b 4 naphth-6-yl)acetyl-1,2,3,4-tetrahydroisoquinoline;
4-(pyrrolidin-1-yl)methyl-5-(1-oxo-3,4-dihydro-(2H)-naphth-6-yl)acetyl-4,5,6,7-tetrahydrothieno [3,2-c]pyridine;
4-(piperidin-1-yl)methyl-5-(1-oxo-3,4-dihydro-(2H)-naphth-6-yl)acetyl-4,5,6,7-tetrahydrothieno [3,2-c]pyridine;
(—)4-piperidin-1-yl)methyl-5-(1-oxo-3,4-dihydro-(2H)-naphth-6-yl)acetyl-4,5,6,7-tetrahydrothieno [3,2-c]pyridine;
(+)4-(piperidin-1-yl)methyl-5-(1-oxo-3,4-dihydro-(2H)-naphth-6-yl)acetyl-4,5,6,7-tetrahydrothieno [3,2-c]pyridine.

The present invention also provides a process for the preparation of a compound of formula I which comprises reacting a compound of formula (III):

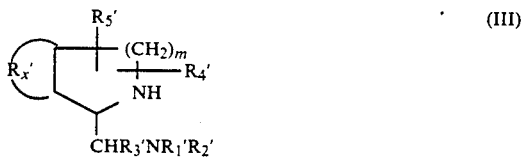

in which $R_1'$, $R_2'$, $R_3'$, $R_5'$ and $R_x'$ are $R_1$, $R_2$, $R_3$, $R_4$, $R_5$ and $R_x$ respectively, as defined for formula (I), or a group or atom convertible to each of $R_1$ to $R_x$, with a compound of formula (IV)

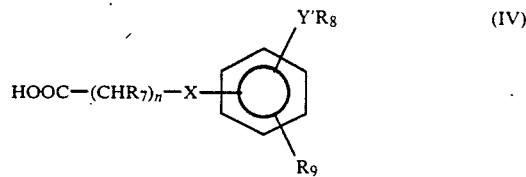

or an active derivative thereof, in which $R_7$, $R_8$, $R_9$, n and X are as defined for formula (I), and Y' is Y or a group convertible to Y;
to form a compound of formula (Ic):

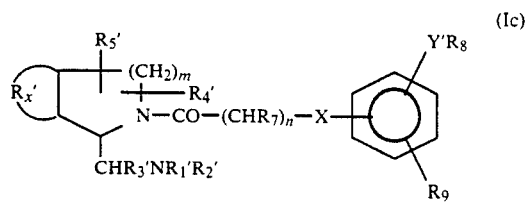

and then optionally performing one or more of the following steps:
a) where Y' and $R_1'$ to $R_x'$ are other than Y and $R_1$ to $R_x$, converting Y' and $R_1'$ to $R_x'$ to Y and $R_1$ to $R_x$ to obtain a compound of formula (I),
b) where Y' and $R_1'$ to $R_x'$ are Y and $R_1$ and $R_x$, converting one of $R_1$ to $R_x$ to another one of $R_1$ to $R_x$ to obtain a compound of formula (I),
c) forming a salt and/or solvate of the obtained compound of formula (I).

Suitable active derivatives of the compound of formula (IV) are acid chlorides or acid anhydrides. Another suitable derivative is a mixed anhydride formed between the acid and an alkyl chloroformate.

For example, in standard methods well known to those skilled in the art, the compound of formula (III) may be coupled:
a) with an acid chloride in the presence of an inorganic or organic base,
b) with the acid in the presence of dicyclohexyl carbodiimide, N-dimethylaminopropyl-N'-ethyl carbodiimide or carbonyl diimidazole,
c) with a mixed anhydride generated in situ from the acid and an alkyl (for example ethyl)chloroformate.

It will be appreciated that a compound of formula (Ic) may be converted to a compound of formula (I), or one compound of formula (I) may be converted to another compound of formula (I), by interconversion of suitable substituents. Thus certain compounds of formula (I) and (Ic) are useful intermediates in forming other compounds of the present invention.

$R_1'$ and $R_2'$ may be alkyl groups and converted to $R_1'$/$R_2'$ hydrogen atoms by conventional amine dealkylation. When $R_1'$ or $R_2'$ is benzyl or substituted benzyl it may be converted to an $R_1$ or $R_2$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The above described process will generally provide a diastereoisomeric mixture which can subsequently separated into isomers by column chromatography.

The compound of formula (IV) is typically of the formula (IVa)

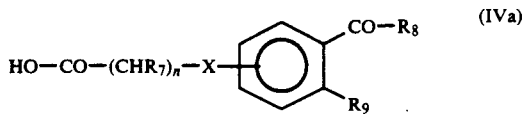

in which $R_8$, $R_9$, $R_7$, X and n are as defined for formula I.

The compounds of formula (I) may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

As mentioned before, the compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

Compounds of formula (III) in which $R_x$ is optionally substituted phenyl may themselves be prepared by treating a compound of formula (V) with an amine of formula $NHR_1' R_2'$ wherein $R_1'$ and $R_2'$ are as defined above) followed by reaction of the formed compound of formula (VI) which $NaBH_4$ or with hydrogen in the presence of a 5% palladium or charcoal catalyst, in accordance with the following reaction Scheme 1:

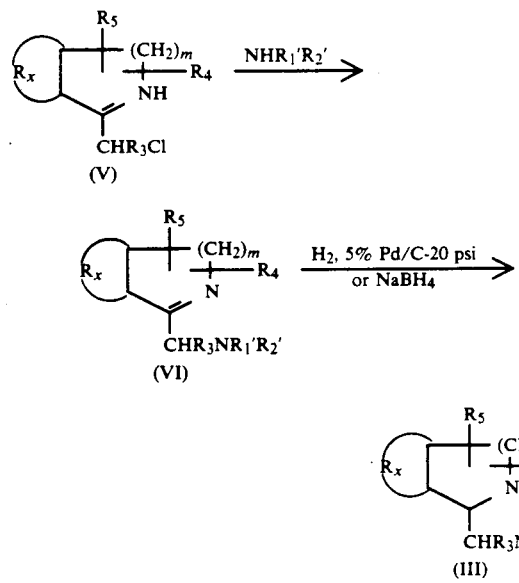

The compounds of formula (V) are known compounds, or can be prepared from known compounds by known methods [see for example J. Am. Chem. Soc. 55, 2555 (1933); J. Org. Chem. 16, 1911 (1951)].

Compounds of formula (III) in which $R_x$ is heterocyclic and $R_3$ is hydrogen may themselves be prepared according to the following reaction Scheme 2:

Scheme 2

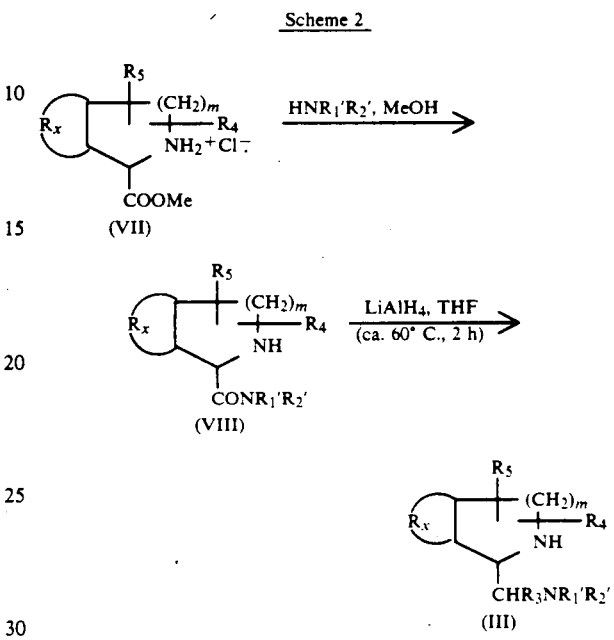

In this reaction scheme, compounds of formula (III) are prepared from compounds of formula (VII) by reaction with secondary amines ($HNR1'R2'$) in a suitable solvent such as methanol, preferably at a temperature of from 0° to 90° C. The obtained compounds of formula (VIII) are then converted to compounds of formula (III) by reduction with a mixed hydride such as $LiAlH_4$, or $(BH_3)_2$, preferably in an inert medium such as THF. A temperature of about 60° C. and a reaction time of about 2 hours has been found to produce advantageous results.

Compounds of formula (VII) are prepared by known methods from known compounds (Heterocycles 16 [n. 1][1981], 35; DE-Al 3529960).

Alternatively compounds of formula (III) in which $R_x$ is heterocyclic and m is 2 can be prepared according to the following reaction Scheme 3:

Scheme 3

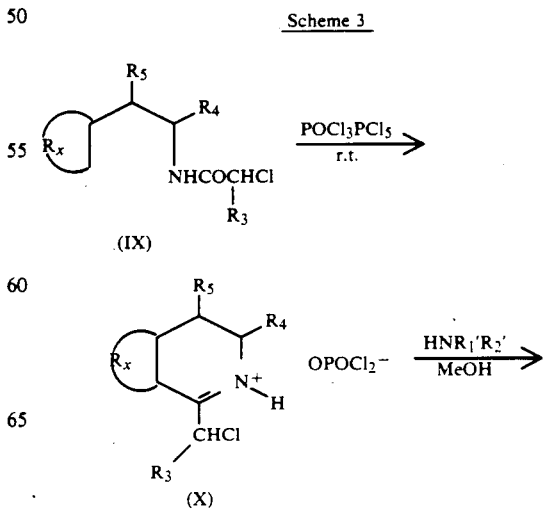

-continued
Scheme 3

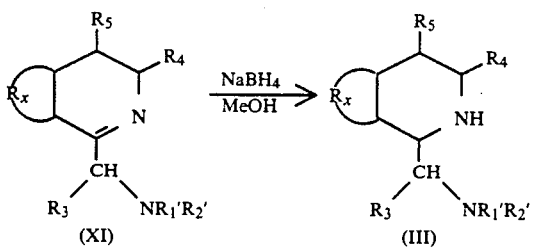

In this reaction scheme compounds of formula (III) are prepared by treating compounds of formula (IX) with phosporus oxychloride and phosphorus pentachloride, at room temperature, followed by filtration of the hygroscopic material. The obtained compounds of formula (X) are then converted to compounds of formula (XI) by reaction with secondary amines HNR1'R2') in a suitable solvent such as methanol, preferably at a temperature of from 0° to 90° C. The compounds of formula (XI) are then treated with a mixed hydride such as $NaBH_4$ or $NaCNBH_3$, preferably in a protic solvent such as methanol, to obtain compounds of formula (III). A temperature of from 0° to 25° C. and a reaction time of about two hours has been found to produce advantageous results.

The compounds of formula (IX) are known compounds, or can be prepared from known compounds by known methods [see for example Synth. Comm. 5 (2), 79 (1975)].

The intermediates of formula III described above are novel compounds and, together with the described processes for their preparation, they form a further aspect of the invention.

The compounds of formula (IV) are known compounds or can be prepared from known compounds by known methods [See, for example J.O.C. 27 (1960), 70–76; Chem. Lett. (1981), 367–370].

The activity of the compounds of formula (I) in standard tests indicates that they are of therapeutic utility in the treatment of pain and of hyponatraemic disease states.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, or in the manufacture of a medicament for the treatment of hyponatraemic disease states.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents or diuretics.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain or as a diuretic.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method for the treatment and/or prophylaxis of pain and/or hyponatraemic disease states in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples, the Description illustrating the preparation of an intermediate.

The compounds of the Examples are summarised in Table I, in which the structure of the group R of formula (II) is identified.

DESCRIPTION 1

1-oxo-3,4-dihydro-(2H)-napht-6-yl acetyl chloride

A solution of 8 g (39 mmoles) of 1-oxo-3,4-dihydro-(2H9-napht-6-yl acetic acid in 400 ml of dry chloroform was cooled to 0° C. and 6.8 ml (7.8 mmoles) of oxalyl chloride were added dropwise.

After 24 hours the solution was evaporated in vacuo and the oily material so obtained was utilized for the subsequent reaction withour further purification.

EXAMPLE 1

1-(pyrrolidin-1-yl)methyl-2-(1-oxo-3,4-dihydro-(2H)-napht-6-Yl)acetyl-1,2,3,4-tetrahydroisoquinoline hydrochloride 1.6 g (7.41 mmoles) of 1-(pyrrolidin-1-yl)methyl-1,2,3,4-tetrahydroisoquinoline were dissolved in 40 ml of dry chloroform. 2.0 g (14.49 mmoles) of anhydrous potassium carbonate were added and the mixture cooled at −10° C. 2.0 g (8.99 mmoles) of crude 1-oxo-3,4-dihydro-(2H)-napht-6-yl acetyl chloride, dissolved in 10 ml of dry chloroform, were added and the reaction mixture allowed to reach room temperature. After one hour 20 ml of water were added and the resulting biphasic solution stirred for additional 30'. The separated organic layer was washed with water, dried over $Na_2SO_4$, concentrated in vacuo. The residue was chromatographed on silica gel eluting with $CH_2CL_2$, containing increasing amounts of MeOH (0.5-3%), to afford 1.1 g of the free base, which was dissolved in 30 ml of acetone, and the solution brought to acidic pH with HCl/diethyl ether. The precipitate was filtered, washed and dried, to yield 700 mg of the title compound.

$C_{26}H_{30}N_2O_2 \cdot HCl$
M.P.=231°-233° C.
M.W.=438.981
Elemental analysis: Calcd. C, 71.13; H, 7.12; N, 6.38; Found C, 70.60; H, 7.26; N, 6.22.
I.R. (KBr): 1685 (m); 1630 (s); 1605 (m) cm−1
N.M.R. ($CDCl_3$) 80 MHz: δ 11.80 (s broad, 1 H); 7.90 (d, 1 H); 6.90–7.40 (m, 6H); 6.10 (d broad, 1H); 3.35–4.40 (m, 7H); 2.35–3.30 (m, 9H); 1.80–2.30 (m,6H).

EXAMPLE 2

1-(piperidin-1-yl)methyl-2-(1-oxo-3,4-dihydro-(2H)-napht-6-yl)acetyl-1,2,3,4-tetrahydroisoquinoline hydrochloride Prepared as Example No. 1 from 1.7 g (7.39 mmoles) of 1-(piperidin-1-yl)methyl-1,2,3,4-tetrahydroisoquinoline, 2.0 g (14.49 mmoles) of anhydrous potassium carbonate and 2.0 g (8.99 mmoles) of crude 1-oxo-3,4-dihydro-(2H)-napht-6-yl acetyl chloride in 50 ml of dry chloroform. The silica gel chromatographic column was eluted with $CH_2Cl_2$, containing increasing amounts of MeOH (0.2-2%), to afford 1.4 g of the pure free base, which was dissolved in 40 ml of ethyl acetate, and the solution brought to acidic pH with HCl/diethyl ether. The precipitate was filtered and recrystallized from acetone, to yield 900 mg of the title compound.

$C_{27}H_{32}N_2O_2 \cdot HCl$
M.P.=146°-148° C.
M.W.=453.007
Elemental analysis: Calcd. C, 71.58; H, 7.34; N, 6.18; Found C, 71.42; H, 7.36; N, 6.14.
I.R. (KBr): 1680 (m); 1645 (s); 1605 (m) cm−1
N.M.R. ($CDCl_3$) 80 Mhz: δ11.10 (s broad, 1H); 7.95 (d, 1H); 6.95–7.35 (m, 6H); 6.10 (dd, 1H); 4.10 (AB system, J=17.5 Hz., 2H); 3.35–4.60 (m, 5H); 2.35–3.15 (m, 9H); 1.60–2.30 (m, 8H).

EXAMPLE 3

4-(pyrrolidin-1-yl)methyl-5-(1-oxo-3,4-dihydro-(2H)-napht-6-yl)acetyl-4,5,6,7-tetrahydrothieno [3,2-c] pyridine hydrochloride Prepared as Example No. 1 from 1.2 g (5.39 mmoles) of 4-(pyrrolidin-1-yl)methyl-4,5,6,7-tetrahydrothieno [3,2-c] pyridine, 1.5 g (10.87 mmoles) of anhydrous potassium carbonate and 1.4 g (6.29 mmoles) of crude 1-oxo-3,4-dihydro-(2H)-napht-6-yl acetyl chloride in 40 ml of dry chloroform. The silica gel chromatographic column was eluted with $CH_2Cl_2$, containing increasing amounts of MeOH (0.5-3%), to afford 1.4 g of the pure free base, which was dissolved in 30 ml of acetone, and the solution brought to acidic pH with HCl/diethyl ether. The precipitate was filtered, washed and dried, to yield 900 mg of the title compound.

$C_{24}H_{28}N_2O_2S \cdot HCl$
M.P.=241°-243° C.
M.W.=445.011

Elemental analysis: Calcd. C, 64.77; H, 6.57; N, 6.30; Found C, 64.33; H, 6.60; N, 6.20.

I.R. (KBr): 1685 (m); 1630 (s); 1605 (m) cm−1

N.M.R. (CDCl3) 80 Mhz: δ11.80 (s broad, 1H); 7.95 (d, 1H); 7.05–7.35 (m, 3H); 6.80 (d, 1H); 6.10 (d broad, 1H); 3.30–4.50 (m, 7H); 2.40–3.25 (m, 9H); 1.80–2.35 (m, 6H);

EXAMPLE 4

4-(piperidin-1-yl)methyl-5-(1-oxo-3,4-dihydro-(2H)-napht-6-Yl)acetyl-4,5,6,7-tetrahydrothieno[3,2-c]pyridine hydrochloride hemihydrate Prepared as Example No. 1 from 1.15 g (4.87 mmoles) of 4- (piperidin-1-yl)methyl-4,5,6,7-tetrahydrothieno [3,2-c]pyridine, 1.4 g (10.14 mmoles) of anhydrous potassium carbonate and 1.3 g (5.84 mmoles) of crude 1-oxo-3,4-dihydro-(2H)-napht-6-yl acetyl chloride in 40 ml of dry chloroform. The silica gel chromatographic column was eluted with CH2Cl2, containing increasing amounts of MeOH (0.2–2%), to afford 700 mg of the pure free base, which was dissolved in 30 ml of ethyl acetate, and the solution brought to acidic pH with HCl/diethyl ether. The precipitate was filtered and recrystallized from acetone to yield 400 mg of the title compound.

$C_{25}H_{30}N_2O_2S.HCl.\frac{1}{2} H_2O$

M.P.=179°–181°60 C.

M.W.=468.045

Elemental analysis: Calcd. C, 64.14; H, 6.79; N, 5.98; Found C, 63.87; H, 6.65; N, 5.83.

I.R. (KBr): 1685 (m); 1635 (s); 1605 (m) cm−1

N.M.R. (CDCl3) 80 Mhz: δ11.70 (s broad, 1H); 7.95 (d, 1H); 7.05–7.40 (m, 3H); 6.75 (d, 1H); 6.10 (d broad, 1H); 3.35–4.60 (m, 7H); 2.30–3.20 (m, 9H); 1.60–2.30 (m, 8H).

EXAMPLE 5

(−)4-(piperidin-1-yl)methyl-5-(1-oxo-3,4-dihydro-(2H)-napht-6-yl)acetyl-4,5,6,7-tetrahydrothieno[3,2-c]pyridine L(+) tartrate 4.0 g (9.46 mmoles) of the compound described in the Example No. 4 (free base) were dissolved in 60 ml of methanol. 1.5 g (9.99 mmoles) of L(+) tartaric acid, dissolved in 20 ml of methanol, were added to the hot solution of the racemate and the mixture gently warmed for 15'. After 24 hours the precipitated diastereoisomeric salt was filtered off and recrystallized several times from MeOH up to a constant rotatory power, to yield 630 mg of the title compound.

$C_{25}H_{30} N_2O_2S.L(+) C_4H_6O_6$

M.P.=205°–207° C.

M.W.=572.660

$[\alpha]_D^{20} = -57.09$ (C=0.5, MeOH)

Elemental analysis: Calcd. C, 60.82; H, 6.34; N, 4.89; Found C, 60.92; H, 6.37; N, 4.88.

80 mg of this salt were treated with NH4OH and extracted with diethyl ether. The organic solution was washed with water, dried over Na2SO4 and the solvent evaporated in vacuo to dryness. The free base gave an $[\alpha]_D^{20} = -96.05$ (C=1,CHCl3)

The I.R. and the N.M.R. spectra of the resolved free base were identical to that obtained for the racemate.

EXAMPLE 6

(+)4-(piperidin-1-yl)methyl-5-(1-oxo-3,4-dihydro-(2H)-napht-6-yl)acetyl-4,5,6,7-tetrahydrothieno[3,2-c]pyridine D(−) tartrate The mother liquours of the first crystallization of Example No. 5 were treated with NH40H and extracted with diethyl ether. The organic solution was washed with water, dried over Na2SO4 and the solvent evaporated in vacuo to dryness. 2.7 g (6.38 mmoles) of the enriched free base were obtained and dissolved in 40 ml of methanol. 1.0 g (6.66 mmoles) of D(−) tartaric acid, dissolved in 30 ml of MeOH, was added to the hot solution and the distereoisomeric salt recrystallized on standing. The salt was filtered off and recrystallized several times from MeOH up to a constant rotatory power, to yield 450 mg of the title compound.

$C_{25}H_{30}N_2O_2S.D(-) C_4H_6O_6$

M.P.=205°–207° C.

M.W.=572.660

$[\alpha]_D^{20} = +57.19$ (C=0.5, MeOH)

Elemental analysis: Calcd. C, 60.82; H, 6.34; N, 4.89; Found C, 61.00; H, 6.40; N, 4.87.

80 mg of this salt were treated with NH4OH and extracted with diethyl ether. The organic solution was washed with water, dried over Nab 2SO4 and the solvent evaporated in vacuo to dryness. The free base gave an $[\alpha]_D^{20} = +95.82$ (C=1, CHCl3)

The I.R. and the N.M.R. spectra of the resolved free base were identical to that obtained for the racemate.

TABLE 1

| Example | R | Molecular Formula | Melting Point (°C.) | [ ] (C = 0.5, MeOH) | [ ] of the corresponding free base (C = 1, CHCl3) |
|---|---|---|---|---|---|
| 1 |  | C26H30N2O2.HCl | 231–233 | — | — |

TABLE 1-continued

| Example | R | Molecular Formula | Melting Point (°C.) | [ ] (C = 0.5, MeOH) | [ ] of the corresponding free base (C = 1, CHCl₃) |
|---|---|---|---|---|---|
| 2 | (isoquinoline-CH₂-N-piperidine structure) | C₂₇H₃₂N₂O₂.HCl | 146–148 | — | — |
| 3 | (thienopyridine-CH₂-N-pyrrolidine structure) | C₂₄H₂₈N₂O₂S.HCl | 241–243 | — | — |
| 4 | (thienopyridine-CH₂-N-piperidine structure) | C₂₅H₃₀N₂O₂S.HCl · ½H₂O | 179–181 | — | — |
| 5 | " | C₂₅H₃₀N₂O₂S. L(+)C₄H₆O₆ | 205–207 | −57.09 | −96.05 |
| 6 | " | C₂₅H₃₀N₂O₂S. D(−)C₄H₆O₆ | 205–207 | +57.19 | +95.82 |

The pharmacological activity of the compounds of this invention is illustrated by the following test procedures.

P-phenylquinone-induced Abdominal Writhinq Test in Mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36 g body weight, are used. Animals are allowed food and water ad libitum and are randomized into groups of 10 prior to experimentation. Test compounds are dissolved in either distilled water or distilled water plus 0.1 M AMS, and administered by the subcutaneous route in a final volume of 10 ml/Kg. Control animals receive 10 ml/Kg of the appropriate vehicle alone. Following a pretreatment period of 20 min., mice are injected intraperitoneally with p-phenylquinone, 2 mg/Kg at 37° C. in a final volume of 10 mg/Kg. Next, the mice are placed, in a groups of 3, in a compartmented perspex box maintained at room temperature and are observed for a period of 8 min. During this period the number of abdominal writhing responses per animal are recorded where writhing consists of an intermittent contraction of the abdomen associated with hind leg extension.

The degree of antinociceptive protection afforded by the test compound is determined as the mean number of writhing responses observed in the treated group (T) expressed as a percentage of the mean number of writhing responses in the control group (C) according to the following formula:

$$[1-(T/C)] \times 100\% = \% \text{ graded protection.}$$

Mouse Tail-flick test (Modified from the procedure published by D Amour et al., J. Pharm. Exptl. Ther.72, 74/1941).

Male Charles River mice, average weight 26g, are used. Selection is carried out before beginning of experiments: only mice whose reaction time is less than 8 sec are used. They are randomly distributed into groups of 10 and dosed with compounds under test, with positive and negative controls being included.

Compounds under test are administered subcutaneously in isotonic saline in a volume of 20 ml. Kg$^{-1}$. 30 min later mice are placed again under heat source (Socrel apparatus) and reaction time is recorded.

The analgesic activity of the test compound is expressed as the percent number of mice doubling the initial time within a group.

$$\% \text{ analgesia} = \frac{\text{No. of mice doubling the reaction time}}{\text{Total no. of mice per group}} \times 100$$

The results are given in Table II

TABLE II

| | ANALGESIA | |
|---|---|---|
| Example | MOUSE WRITHING ED50 (mg/Kg s.c.) | MOUSE TAIL-FLICK ED50 (mg/Kg s.c.) |
| 1 | 0.036 | 0.114 |
| 2 | 0.038 | 0.206 |
| 3 | 0.023 | 0.086 |
| 4 | 0.017 | 0.174 |

TABLE II-continued

| | ANALGESIA | |
|---|---|---|
| Example | MOUSE WRITHING ED50 (mg/Kg s.c.) | MOUSE TAIL-FLICK ED50 (mg/Kg s.c.) |
| 5 | 0.009 | 0.045 |

All data are given for the compounds in free base form.

We claim:

1. A compound, or a solvate or salt thereof, of formula (I):

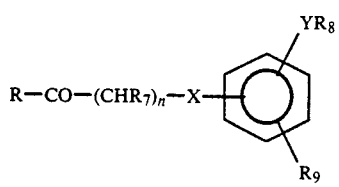

in which R represents a group of formula (II)

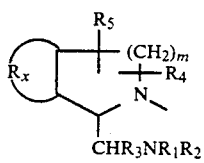

in which $R_x$ together with the carbon atoms to which it is attached forms thienyl, furyl, pyrryl, imidazolyl, pyrazolyl, thiazolyl, pyridyl, or an optionally substituted phenyl group;

$R_1$ and $R_2$ are idependently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene which may additionally contain an oxygen or sulphur or $C_{2-6}$ alkenylene group;

$R_3$ is hydrogen, $C_{1-6}$ alkyl, or phenyl, or $R_3$ together with $R_1$ form a $—(CH_2)_3—$ or $—(CH_2)_4—$ group;

$R_4$ and $R_5$, which may be located on the same or different carbon atoms, are independently hydrogen, $C_{1-6}$ alkyl, or phenyl;

m is 2;

$R_7$ is hydrogen or $C_{1-6}$ alkyl;

n is 0, 1 or 2;

X is direct bond, or O, S, or $NR_6$ in which $R_6$ is hydrogen or $C_{1-6}$ alkyl;

Y is $>C=O$, $>CHOH$, $>S=O$ or $>SO_2$ each of $R_6$ and $R_9$ is $C_{1-6}$ alkyl, or $R_8$ and $R_9$ are linked together and $R_8$ represents $—(Z—)_p—$ where p is 0 or 1 and Z is O, S or $NR_z$ where $R_z$ is hydrogen or $C_{1-6}$ alkyl; and $R_9$ represents $—(CH_2)_q—$ where q is an integer of from 1 to 4.

2. A compound according to claim 1 in which each of $R_1$ and $R_2$ is methyl, ethyl, propyl, butyl, pentyl or hexyl.

3. A compound according to claim 1, in which $R_1$ and $R_2$ together form a propylene, butylene, pentylene or hexylene group, or a $—CH_2—CH=CH—CH_2—$ group.

4. A compound according to claim 1 in which $R_x$ is thienyl, furyl, pyrryl, imidazolyl, pyrazolyl, thiazolyl, or pyridyl.

5. A compound according to claim 1 which is of formula (Ia):

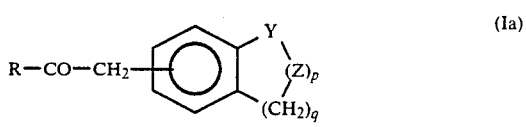

in which R, Y, Z, p and q are as defined in formula (I).

6. A compound according to claim 1 which is of formula (Ib):

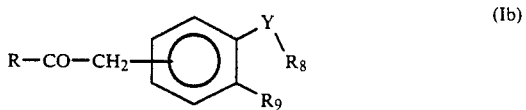

in which R as defined in formula (I); Y is $C=O$ or $—CHOH$ and each of $R_8$ and $R_9$ is $C_{1-6}$ alkyl.

7. A compound selected from the group consisting of:
1-(pyrrolidin-1-yl)methyl-2-(1-oxo-3,4-dihydro-(2H)-naphth-6-yl)acetyl-1,2,3,4-tetrahydroisoquinoline;
1-(piperidin-1-yl)methyl-2-(1oxo-3,4-dihydro-(2H)-naphth-6-yl)acetyl-1,2,3,4-tetrahydroisoquinoline;
4-(pyrrolidin-1-yl)methyl-5-(1-oxo-3,4-dihydro-(2H)-naphth-6-yl)acetyl-4,5,6,7-tetrahydrothieno [3,2-c]pyridine;
4-(piperidin-1-yl)methyl-5-(1-oxo-3,4-dihydro-(2H)-naphth-6-yl)acetyl-4,5,6,7-tetrahydrothieno [3,2-c]pyridine;
(−)4-(piperidin-1-yl)methyl-5-(1-oxo-3,4-dihydro-(2H)-naphth-6-yl)acetyl-4,5,6,7-tetrahydrothieno [3,2-c]pyridine;
(+)4-(piperidin-1-yl)methyl-5-(1-oxo-3,4-dihydro-(2H)-naphth-6-yl)acetyl-4,5,6,7-tetrahydrothieno [3,2-c]pyridine.

8. A pharmaceutical composition comprising a compound according to claim 1, and a pharmaceutically acceptable carrier.

9. A composition according to claim 8 in unit dosage form.

10. A method for the treatment pain and/or hyponatraemic disease states in mammals, which comprises administering to the mammal in need of such treatment an effective amount of a compound of formula (I), as defined in claim 1, or a pharmaceutically acceptable salt or solvate thereof.

* * * * *